(12) United States Patent
Dooling

(10) Patent No.: US 7,057,808 B2
(45) Date of Patent: Jun. 6, 2006

(54) SLIDE STAINING DEVICE

(76) Inventor: Scott E. Dooling, Rt. 3 Box 3050, Paris, TX (US) 75461

( * ) Notice: Subject to any disclaimer, the term of this patent is extended or adjusted under 35 U.S.C. 154(b) by 114 days.

(21) Appl. No.: 10/778,581

(22) Filed: Feb. 17, 2004

(65) Prior Publication Data

US 2005/0179999 A1    Aug. 18, 2005

(51) Int. Cl.
G01N 1/28    (2006.01)
(52) U.S. Cl. .................... 359/398; 356/244
(58) Field of Classification Search ........ 359/396–398;
206/456; 427/2.11; 435/40.5, 40.51, 40.52,
435/288.3–288.7, 305.1; 73/864.51, 864.91;
40/701; 356/244, 246
See application file for complete search history.

(56) References Cited

U.S. PATENT DOCUMENTS

| | | | |
|---|---|---|---|
| 2,262,058 A | 11/1941 | Sinclair | 40/649 |
| 2,633,980 A | 4/1953 | Jorgensen | 206/456 |
| 2,761,558 A | 9/1956 | McLean | 206/456 |
| 2,942,520 A * | 6/1960 | Rose | 359/398 |
| 3,746,161 A | 7/1973 | Jones | 206/456 |
| 3,756,393 A | 9/1973 | Markwitz et al. | 206/456 |
| 4,039,247 A * | 8/1977 | Lawman et al. | 359/398 |
| 4,336,765 A * | 6/1982 | Coughlin | 118/50 |
| 4,819,804 A | 4/1989 | Levy | 206/456 |
| 4,828,111 A | 5/1989 | Rosenberg | 206/456 |
| 5,595,710 A | 1/1997 | Van Dusen et al. | 422/104 |
| 5,958,341 A * | 9/1999 | Chu | 422/99 |
| 6,118,582 A * | 9/2000 | Del Buono | 359/398 |
| 6,899,288 B1 * | 5/2005 | Filicicchia et al. | 239/424 |
| 2004/0114227 A1 * | 6/2004 | Henderson et al. | 359/391 |
| 2005/0136534 A1 * | 6/2005 | Austin et al. | 435/287.2 |

* cited by examiner

Primary Examiner—Mark A. Robinson
Assistant Examiner—Lee Fineman
(74) Attorney, Agent, or Firm—Richard C. Litman

(57) ABSTRACT

The slide staining device has a generally rectangular body which includes an upper rectangular frame and a lower rectangular frame. The upper rectangular frame and the lower rectangular frame are aligned and detachably connected together so that multiple microscope slides may be clamped therebetween for staining at the same time. Knobs with threaded bolts projecting therefrom fasten the upper and lower frames together. The lower rectangular frame includes a plurality of ridges to allow for liquid drainage during the washing stage of a staining procedure and a handle to facilitate manipulation of the device. The device of the present invention is designed to complement established and standard laboratory practice.

4 Claims, 3 Drawing Sheets

SLIDE STAINING DEVICE

BACKGROUND OF THE INVENTION

1. Field of the Invention

The present invention relates to a device for staining microscope slides, and more particularly, to a device which allows for manual staining of multiple microscope slides at one time.

2. Description of the Related Art

In the biological arts, the investigation of living tissues and fluids for structure and possible pathology has long proceeded with the aid of microscopic investigation. Specifically, samples of tissues and fluids have classically been placed upon small rectangular glass plates, known as slides, which are then placed under a microscope or similar magnifying device where visible structural characteristics may be viewed. In connection with microscopic investigations, the employment of staining compositions was introduced to aid in the identification process. Staining increases the contrast for a microscopic examination, making structures in cells or tissues visible in differentiated fashion. Present manual staining processes typically involve dipping individual slides into small vats or jars containing the chemicals and/or dyes. A severe drawback of the presently used techniques is that they include labor intensive steps which require individual manual handling of the slides, such as transferring individual slides from a slide rack to the vats or jars, drying each slide and replacing each slide back in the rack. Thus, the presently used manual staining techniques are tedious and time consuming. Automated systems for specimen staining have been introduced but have not gained widespread acceptance due to their high cost and requirements for adopting new procedures.

U.S. Pat. No. 6,118,582, issued Sep. 12, 2000 to S. Carlos Del Buono, discloses a slide holder for receiving one or more microscope slides. The slide holder includes a generally rectangular frame and at least one slot, each of the slots for receiving one slide. Flexible retaining latches and retaining grooves are provided at each of the slots for facilitating the securing of the slides.

U.S. Pat. No. 3,746,161, issued Jul. 17, 1973 to W. E. Jones, discloses a holder for flat rectangular objects, such as microscope slides. The holder includes a base with upstanding elongated sidewalls and transverse end walls to form a major elongated receptacle. The elongated receptacle is divided into individual smaller receptacles by a plurality of vertical partitions. Each smaller receptacle includes an abutment at one end adjacent to the corresponding sidewall and an opening at an opposing end which is defined in the base. A slide can be placed on the base between adjacent partitions with one end of the slide engaging an abutment and the other end extending partially over a corresponding opening in the base.

Other related patents include U.S. Pat. No. 2,262,058, issued Nov. 11, 1941 to J. G. Sinclair (slide holder); U.S. Pat. No. 2,633,980, issued Apr. 7, 1953 to J. V. Jorgensen (microscope slide holder); U.S. Pat. No. 2,761,558, issued Sep. 4, 1956 to J. D. McLean Jr. (holder for microscope slides); U.S. Pat. No. 3,756,393, issued Sep. 4, 1973 to B. Markwitz et al. (container for object slides); U.S. Pat. No. 4,819,804, issued Apr. 11, 1989 to A. Levy (slide holder); U.S. Pat. No. 4,828,111, issued May 9, 1989 to J. H. Rosenberg (container for holding packages for cover glass and individual glass slides); and U.S. Pat. No. 5,595,710, issued Jan. 21, 1997 to J. M. Van Dusen (medical slide holder).

None of the above inventions and patents, taken either singly or in combination, is seen to describe the instant invention as claimed. Thus a slide staining device solving the aforementioned problems is desired.

SUMMARY OF THE INVENTION

The slide staining device of the present invention has a generally rectangular body having an upper rectangular frame and a lower rectangular frame. The upper rectangular frame and the lower rectangular frame are aligned and detachably connected together so that multiple microscope slides may be clamped therebetween for staining at the same time. Knobs with threaded bolts projecting therefrom fasten the upper and lower frames together. The lower rectangular frame includes a plurality of ridges to allow for liquid drainage and a handle to allow for easy manipulation of the device while transporting the slides and during the washing stage of a staining procedure. The device of the present invention is designed to complement established and standard laboratory practice.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
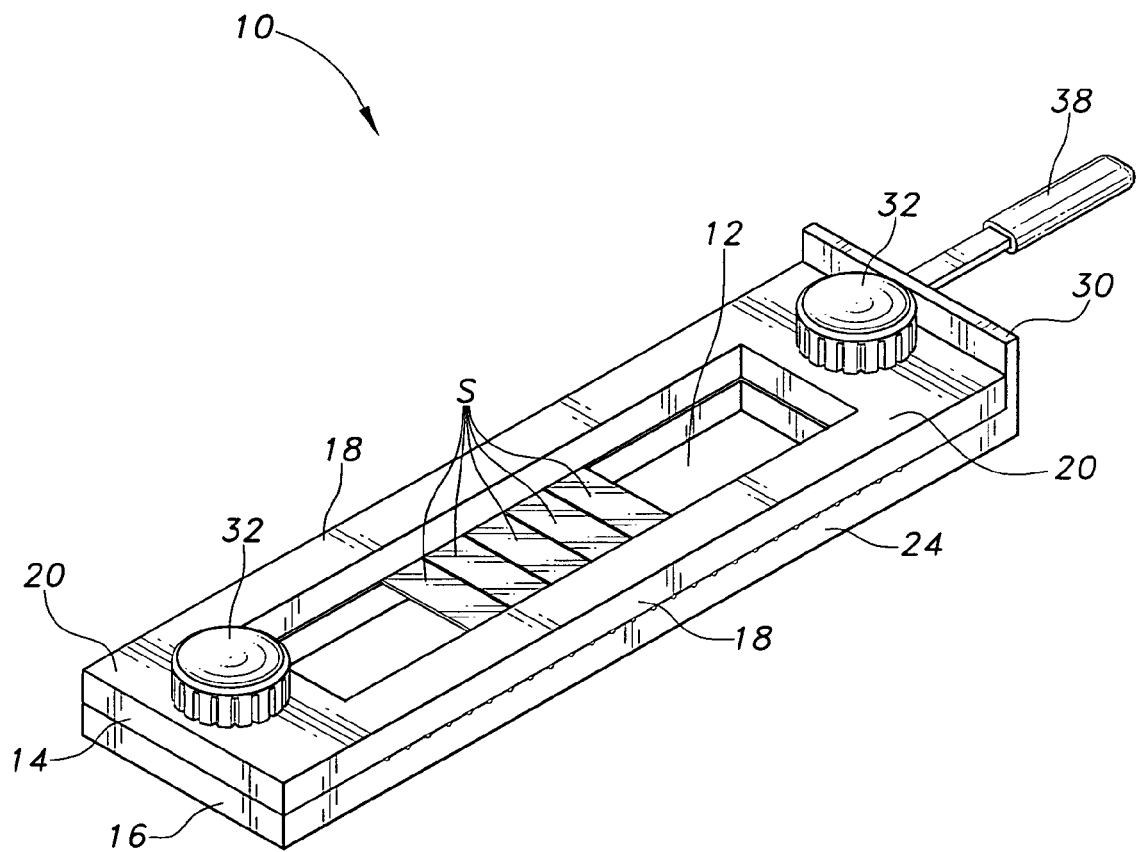
FIG. 1 is an environmental, perspective view of a slide staining device according to the present invention.

The present invention relates to a slide staining device, generally designated as 10 in the drawings. As can be seen from FIG. 1, the device 10 is generally rectangular and includes a central open area 12 in which one or more conventional microscope slides S may be mounted for staining. The device 10 has an upper rectangular frame 14 and a lower rectangular frame 16. The upper and lower frames, 14 and 16, can be made from any suitable chemically resistant material. Preferably, the upper and lower frames, 14 and 16, are made from metal or a high density plastic material.

Figure 2:
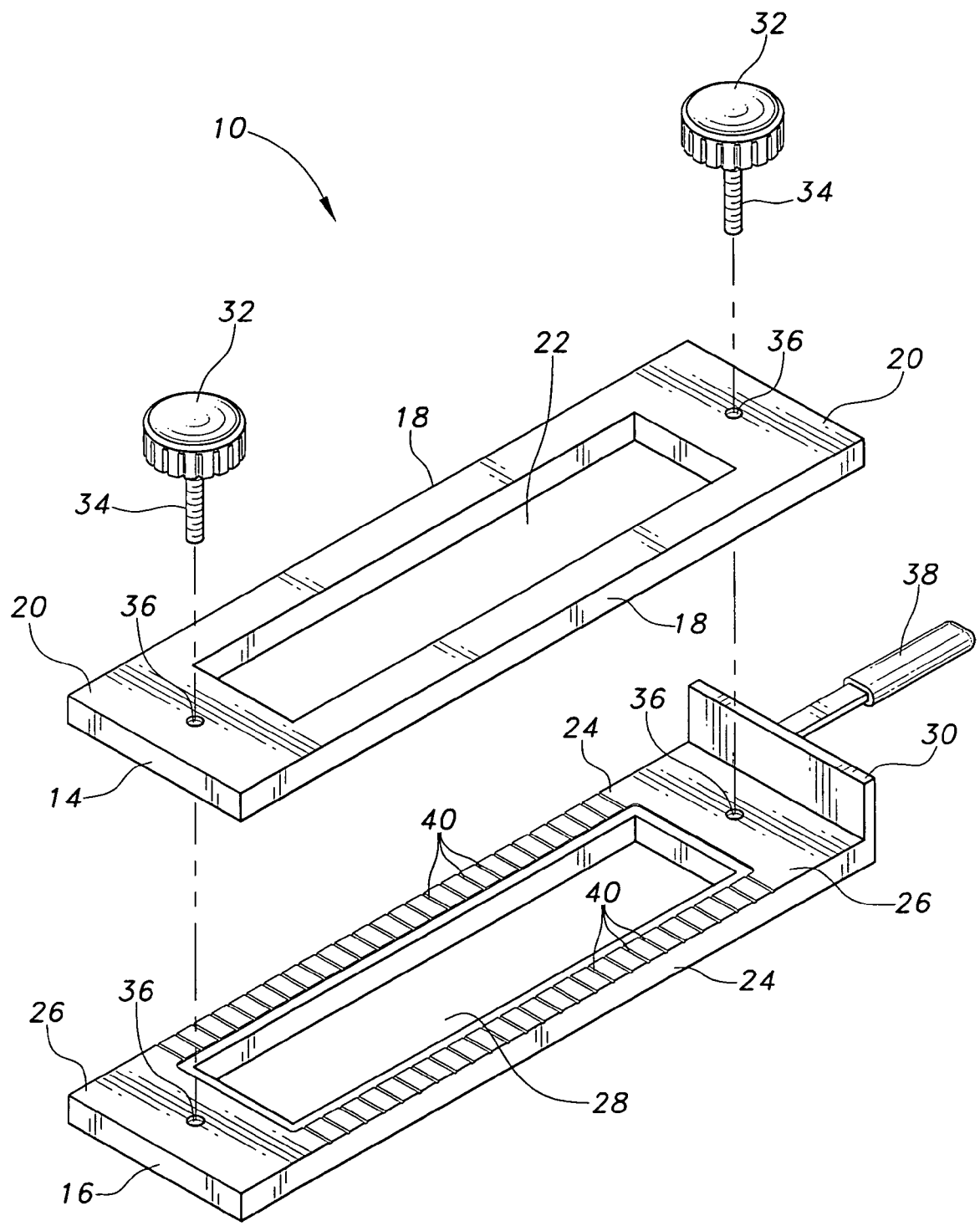
FIG. 2 is an exploded view of the slide staining device according to the present invention.

As can be seen more clearly in FIG. 2, the upper frame 14 is defined by a pair of parallel, opposing upper support ledges 18 and a pair of parallel, opposing upper side members 20. The upper side members 20 extend between and join opposite ends of the support ledges 18 to define an upper open area 22. Similarly, the lower frame 16 is defined by a pair of parallel, opposing lower support ledges 24 and a pair of parallel, opposing lower side members 26. The lower side members 26 extend between and join at opposite ends of the lower support ledges 24 to define a lower open area 28. A flange 30 extends vertically from one of the lower side members 26. Preferably, the upper support ledges 18 are wider than the lower support ledges 24, making the upper open area 22 slightly narrower than the lower open area 28.

As shown in FIG. 2, the upper and lower rectangular frames 14 and 16 are joined by disposing the upper frame 14 over the lower frame 16 such that the upper and lower frames, 14 and 16, are in substantial alignment. When the upper and lower frames, 14 and 16, are disposed in this manner, the flange 30 abuts one of the upper side members 20 of the upper frame 14. The upper open area 22 and the lower open area 28, when aligned, together define the general open area 12 in which slides S may be mounted. Retention knobs 32 are connected to the upper and lower side members 20 and 26 at opposite ends of the frames 14 and 16 to releasably connect the upper and lower frames 14 and 16, respectively, together, thereby clamping the microscope slides S therebetween. Preferably, the knobs 32 have threaded bolts 34 projecting therefrom which are received by threaded apertures 36 defined in the upper and lower side members 20 and 26, respectively. Alternatively, the lower frame 16 may have externally threaded studs extending from side members 26 that extend through apertures defined in the side members 20 of upper frame 14 and mate with internally threaded bores defined in knobs 32 to clamp the frames 14 and 16 together.

A handle 38, which extends horizontally from the flange 30, is provided to facilitate handling of the device 10 when the upper and lower frames, 14 and 16, are secured together. A plurality of ridges 40 are defined across the width of the upper surface of the lower support ledges 24 to allow for water drainage during the washing stage of staining.

Figure 3:
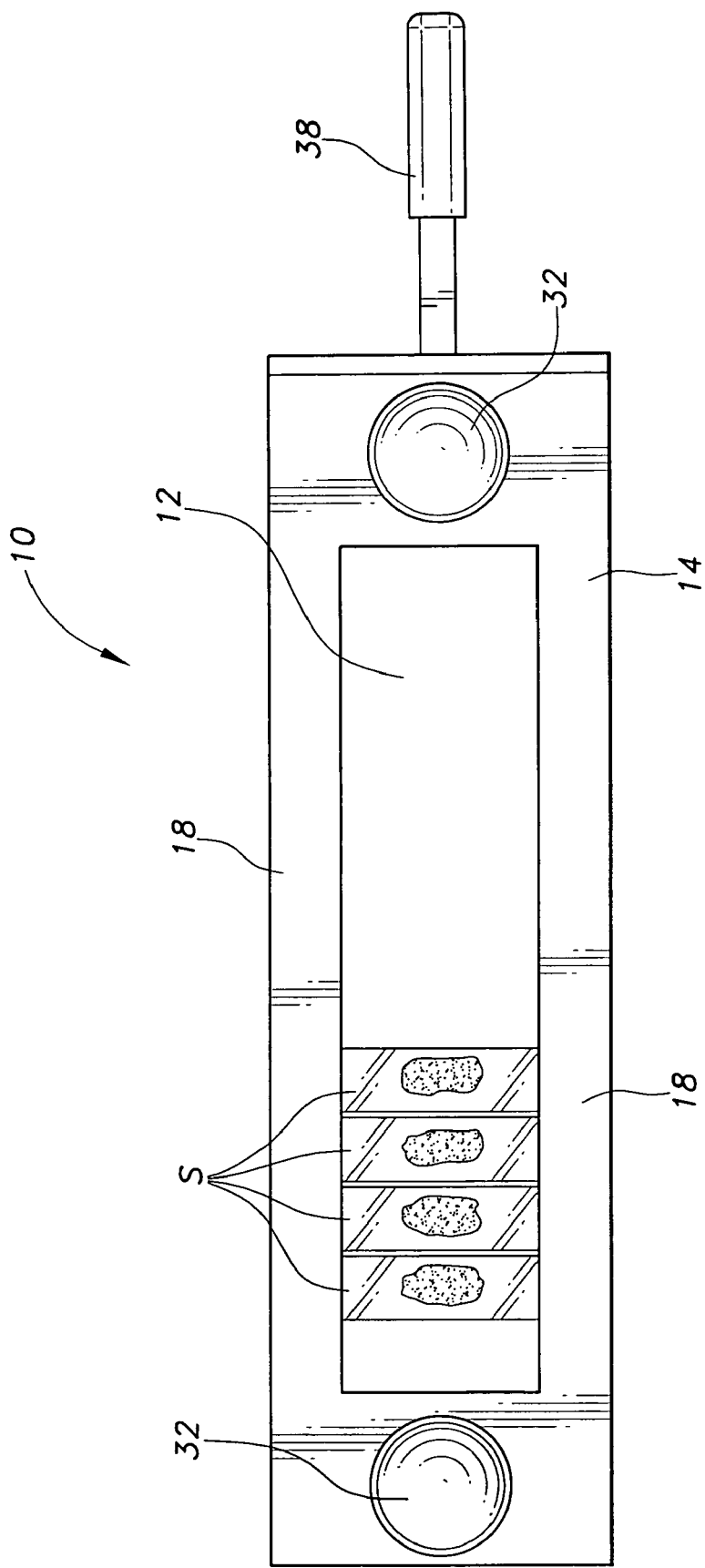
FIG. 3 is a plan view of the slide staining device according to the present invention.

By adjusting the knobs 32 accordingly, a user may join or detach the upper and lower frames, 14 and 16. When the knobs 32 are loosened, one or more conventional microscope slides S may be inserted between the upper and lower support ledges 18 and 24, as shown in FIGS. 1 and 3, or removed therefrom. When the knobs 32 are tightened, the ends of the slides S are clamped between the upper and lower support ledges, 18 and 24, as shown in FIG. 3. Once the slides S are secured to the device 10, the device 10 may be used to stain, transport, or wash multiple slides without having to secure each slide S to a support individually between stainings.

It is to be understood that the present invention is not limited to the embodiment described above, but encompasses any and all embodiments within the scope of the following claims.

I claim:

1. A slide staining device for supporting and clamping a plurality of microscope slides for staining, said slide staining device comprising:
    an upper rectangular frame having a pair of parallel, elongate, opposing upper support ledges and a pair of parallel, opposing upper side members joined together to define a generally rectangular central upper open area having a length and a width;
    a lower rectangular frame having a pair of parallel, elongate, opposing lower support ledges and a pair of parallel, opposing lower side members joined together to define a generally rectangular central lower open area having a length and a width;
    a plurality of ridges defined on and extending across each of said lower support ledges;
    a flange extending vertically upward from one of said lower side members;
    an elongate handle extending horizontally from said flange;
    a pair of knobs, each of the knobs having a threaded bolt extending therefrom, the bolts extending through each of the upper side members and being removably secured to each of the lower side members;
    whereby said upper and lower rectangular frames are configured to support and clamp a plurality of side-by-side, horizontally aligned microscope slides between said upper and lower parallel ledges, said upper and lower parallel ledges configured to engage each microscope slide of said plurality of horizontally aligned slides when said bolts on said knobs are extended through each of the upper side members and are removably secured to each of said lower side members.

2. The slide staining device according to claim 1, wherein each of said lower side members has a threaded aperture defined therein for receiving said bolts.

3. The slide staining device according to claim 2, wherein each of said upper side members has a threaded aperture defined therein, the threaded apertures in the upper and lower side members being aligned when said knobs clamp the upper frame to the lower frame.

4. The slide staining device according to claim 1, wherein the width of the generally rectangular central upper open area is narrower than the width of the generally rectangular central lower open area.

* * * * *